United States Patent [19]

Ostermaier

[11] 4,416,825

[45] Nov. 22, 1983

[54] PREPARATION OF ZEROVALENT NICKEL COMPLEXES

[75] Inventor: John J. Ostermaier, Orange, Tex.

[73] Assignee: E. I. Du Pont de Nemours & Co., Wilmington, Del.

[21] Appl. No.: 351,421

[22] Filed: Feb. 23, 1982

[51] Int. Cl.³ .............................................. C07F 15/04
[52] U.S. Cl. ................................................. 260/439 R
[58] Field of Search ..................... 260/439 R

[56] References Cited

U.S. PATENT DOCUMENTS

| | | | |
|---|---|---|---|
| 3,102,899 | 9/1963 | Cannell | 260/439 R |
| 3,152,158 | 10/1964 | Clark | 260/439 R |
| 3,328,443 | 6/1967 | Clark et al. | 260/439 R |
| 3,346,608 | 10/1967 | Von Kutepow et al. | 260/439 R |
| 3,631,191 | 12/1971 | Kane et al. | 260/439 R |
| 3,668,086 | 6/1972 | Hughes | 260/439 R X |
| 3,671,560 | 6/1972 | Fahey | 260/439 R X |
| 3,903,120 | 9/1975 | Shook, Jr. et al. | 260/439 R |
| 4,055,582 | 10/1977 | Fahey | 260/439 R |

*Primary Examiner*—Helen M. S. Sneed

[57] ABSTRACT

An improved, continuous process for the preparation of hydrocyanation catalysts comprising zerovalent nickel complexes with organophosphorus compounds (ligands) by controlling the temperature of the reaction relative to the amount of ligand and conducting the reaction in the presence of a chlorine ion and organic nitrile such as adiponitrile.

6 Claims, No Drawings

PREPARATION OF ZEROVALENT NICKEL COMPLEXES

BACKGROUND OF THE INVENTION

1. Field of the Invention

The present invention is directed toward the continuous preparation of zerovalent nickel complexes and more particularly, to the continuous preparation of complexes of the formula $Ni(L)_4$ where L is an organophosphorus containing ligand.

2. Description of the Prior Art

The general chemistry for the preparation of zerovalent nickel catalysts by reacting finely divided nickel powder and certain ligands in the presence of an organochloridite and nitrile solvent is described in U.S. Pat. No. 3,903,120 issued on Sept. 2, 1975 to H. F. Shook et al. The present invention is an improvement upon the invention described in the aforementioned patent.

SUMMARY OF THE INVENTION

An improved process for the continuous production of a zerovalent nickel complex having the general formula $Ni(L)_4$ and L is a neutral ligand, e.g., a ligand having the formula $P(OAr)_3$ where Ar is an aryl group of up to 18 carbon atoms which comprises or consists of continuously contacting elemental nickel having a surface area of at least about 800 square centimeters per gram of nickel, in a reaction medium containing or comprising in percent by weight based upon the weight of the liquid in the reaction medium at least 50% L, at least 2% of an organic nitrile having 4-20 carbon atoms and at least 100 ppm Cl as an organochloridite while maintaining the temperature in °C. of the reaction within the range defined by a minimum temperature equal to $102 - 0.375 \times (\%L)$ and a maximum temperature equal to $58.3 + 0.725 \times (\%L)$ and continuously recovering reaction product after separating any unreacted nickel therefrom.

DETAILED DESCRIPTION OF THE INVENTION

The catalysts to which the process of the present invention is applied are zerovalent complexes of nickel with a ligand, L, which ligand is further defined by the formula $PZ_3$ where Z is R or OR and R is an alkyl or aryl group having up to 18 carbon atoms. Of particular interest are ligands of the formula $P(OAr)_3$ where Ar is an aryl group of up to 18 carbon atoms. Illustrative of the aryl groups are methoxyphenyl, tolyl, xylyl and phenyl. Meta- and para-tolyl and mixtures thereof are the preferred aryl groups.

The above nickel complexes are used as catalysts, e.g., in the hydrocyanation of any non-conjugated, ethylenically unsaturated organic nitrile of from 4 to 20 carbon atoms and particularly in the hydrocyanation of pentenenitriles, e.g., cis- and trans-3-pentenenitrile (3PN), 4-pentenenitrile (4PN) and mixtures thereof (3,4-PN's) to produce adipontrile (ADN) which in turn is used to produce polyhexamethyleneadipamide, a commercial polyamide useful in forming fibers, films and molded articles.

Since the processes which employ these nickel catalysts are conducted continuously, it is preferred to prepare the catalyst in a continuous manner. It has been discovered that certain variables have a pronounced effect on the productivity of the catalyst preparation system and interact so that certain unobvious constraints must be applied to realize acceptable productivity. The variables which have the most pronounced effect on productivity are reaction temperature and ligand and solvent concentration. The surface area of the nickel powder introduced into the system and the concentration of the chloridite catalyst must also be controlled if acceptable productivity is to be realized. A productivity below about $4.0 \times 10^{-3}$ pounds per hour per gallon of reaction medium is not acceptable.

The concentration of ligand in the reaction must be maintained within certain limits because productivity rapidly decreases if too much or too little ligand is present. Generally at least 50% and usually 65-90% by weight based upon the weight of the liquid (excludes nickel powder) in the reaction medium of ligand must be present so that some variance in the reaction conditions can be tolerated while maintaining acceptable productivity. As the concentration of ligand is increased above 50% the productivity of the system increases until a maximum productivity is realized at about 88-92% ligand whereupon the productivity begins to decrease with increasing concentration of ligand. When the ligand concentration reaches about 98% the productivity is barely acceptable and roughly corresponds to that realized when 50% ligand is present. It is preferred to conduct the present process at a ligand concentration of about 70-92%.

The temperature is a second major variable in the present process. Unlike many reactions which can be accelerated by increasing the temperature it has been discovered that the productivity of the present reaction increases rapidly with increasing temperature until the productivity reaches a maximum. Further increase in temperature results in a rapidly decreasing productivity. In addition, it has been found that the temperature at which the maximum rate is realized, as well as the minimum and maximum temperatures for acceptable reaction rates, are dependent upon the concentration of ligand in the reaction medium. The minimum temperature ($T_{min}$) at which an acceptable productivity can be obtained is defined by the equation: $T_{min}$ (°C.) $= 102 - 0.375 \times (\%L)$ while the maximum temperature ($T_{max}$) at which an acceptable productivity can be obtained is defined by the equation: $T_{max}$ (°C.) $= 58.3 + 0.725 \times (\%L)$. The temperture at which the highest productivity is realized for a given concentration of ligand is approximately midway between $T_{min}$ and $T_{max}$. Thus, productivity can be maximized by controlling the temperature relative to or along with the concentration of ligand in the reaction medium.

A nitrile solvent must be present in the reaction medium if acceptable productivity is to be obtained according to the foregoing considerations. Mononitriles e.g., any non-conjugated ethylenically unsaturated organic nitrile having from 4 to 20 carbon atoms and especially 3-PN, 4-PN and 3-,4-PN's can be used as the nitrile solvent. Dinitriles, especially the hydrocyanation products of the above-described mononitriles, e.g., adiponitrile, methylglutaronitrile and ethylsuccinonitrile, are also effective solvents. Although usually from 6-12% and preferably 8-11% by weight based upon the weight of liquid in the reaction medium of the nitrile is employed, as little as 2% can be used provided that other variables are maintained at or quite near to their optimum values. Concentration of solvent in excess of about 20% is not preferred.

In order to obtain acceptable productivity, a catalyst for the nickel reaction must also be present in addition to the nitrile solvent. Suitable catalysts include organochloridites of the formula $(R'O)_x R''_y PX$ where $R'$ and $R''$ are alkyl or aryl radicals having up to 18 carbon atoms, being either the same or different, x and z are 1-2, y is 0 or 1 and the sum of x, y and z is 3 and wherein x is a halide selected from the group consisting of chloride, bromide and iodide. The catalyst can be performed or prepared in situ by reaction of an appropriate ligand, L, having at least two ROP linkages with a suitable halide source as an initiator such as a halide or alkyl-substituted halide of phosphorus, e.g., $CH_3PCl_2$. Other compounds useful in forming these chloridites are obvious to those skilled in the art. At least about 100 and preferably 150-300 ppm Cl as chloridite (based upon the weight of liquid in the reaction) must be present to be effective. More than 300 ppm can be employed but the benefits of such higher levels are questionable.

The nickel metal should be introduced into the reaction in finely divided form so as to provide a high surface area for reaction but the particle size should not be so small that difficulties are encountered in separating the unreacted nickel from the reaction product. The surface area should be at least 800 and preferably 800-2000 square centimeters per gram of nickel. Suitable sources for nickel include the "Chemical Grade" nickels sold by International Nickel Company. It is preferred to employ an excess of nickel the amount of which is dependent upon the particle size and surface area, i.e., the reactivity of the nickel. Generally, 4-10 fold excess can be employed but little advantage is realized by employing more than the aforementioned amounts.

The catalyst prepared according to the foregoing teachings when used in the continuous hydrocyanation of unsaturated mononitriles such as 3-,4-PN's is only partially depleted. The catalyst is recovered from the hydrocyanation reaction product preferably by an extraction process such as that described in U.S. Pat. No. 3,773,809 issued on Nov. 20, 1973 and after removal of spent catalyst, this partially depleted catalyst is again reacted with nickel powder according to the process of the present invention. The renewed catalyst is then returned to the hydrocyanation. The following Examples are presented to illustrate but not to restrict the present invention. Parts and percentages are by weight unless otherwise noted.

EXAMPLE I

In order to simulate conditions wherein the present process is operated continuously while receiving partially depleted recycle catalyst, a solution of the approximate composition of the recycle stream is prepared containing 10.5 moles of a mixture of meta- (70%) and para- (30%) tritolylphosphite (TTP) for each mole of zerovalent nickel, at an 80% TTP concentration, 200 ppm Cl as meta- (70%), para- (30%) ditolylphosphorochloridite and 18% 3-PN solvent according to the teachings of U.S. Pat. No. 3,903,120—Example 1-A. This solution is continuously introduced into a stirred reactor. The contents of the reactor are maintained at the temperature indicated in the Table with a steam jacket and the feed rate adjusted to provide a holdup time of 10 hours. Nickel powder having a surface area of 1300 cm$^2$/gram of nickel is added to maintain a concentration of 6 g Ni powder/100 g liquid. The nickel powder is produced by the thermal decomposition of nickel carbonyl at 200° C., which produces a high purity product. Such nickel powder is sold under the brand name INCO 123. The liquid product is separated from the nickel powder by centrifugation with the nickel solids being returned to the reactor. The rate of production of soluble zerovalent nickel is given in the Table.

EXAMPLE II-V

Example I is repeated except that the reaction temperature is varied. The results are reported in the Table.

TABLE

| Example No. | Temperature (°C.) | Productivity (lbs/hour-gal) $(10^{+3})$ |
|---|---|---|
| 1 | 95 | 8.0 |
| 2 | 72 | 4.2 |
| 3 | 116 | 4.5 |
| 4 | 85 | 6.7 |
| 5 | 105 | 7.3 |

EXAMPLE VI

Example I is repeated, except the TTP concentration in the reactor feed is 60 wt %, and the pentenenitrile solvent concentration is 38 wt %. The productivity is $5.4 \times 10^{-3}$ lb/hr-gal.

EXAMPLE VII

Example I is repeated, except the TTP concentration in the reactor feed is 90 wt % and the penetenenitrile solvent concentration is 8.0 wt %. The productivity is $8.6 \times 10^{-3}$ lb/hr-gal.

EXAMPLE VIII

Example I is repeated, except the TTP concentration in the reactor feed is 96 wt % and the pentenenitrile solvent concentration is 2 wt %. The productivity is $4.1 \times 10^{-3}$ lb/hr-gal.

EXAMPLE IX

Example I is repeated, except the chloridite concentration in the reactor feed is 100 ppm Cl. The productivity is $6.2 \times 10^{-3}$ lb/hr-gal.

COMPARATIVE I

Example I is repeated, except the TTP concentration in the reactor feed is 98 wt % and the pentenenitrile solvent concentration is 0 wt %. The productivity is $0.9 \times 10^{-3}$ lb/hr-gal.

COMPARATIVE II

Example I is repeated, except the chloridite concentration in the reactor feed is 50 ppm Cl. The productivity is $1.3 \times 10^{-3}$ lb/hr-gal.

COMPARATIVE III

Example I is repeated, except the nickel powder surface area is 20 cm$^2$g solution. The productivity is $3.5 \times 10^{-3}$ lb/hr-gal.

I claim:

1. An improved process for the continuous production of a zerovalent nickel complex having the general formula Ni(L)$_4$ where L is a neutral ligand of the formula P(Z)$_3$ where Z is R or OR and R is an alkyl or an aryl group of up to 18 carbon atoms which comprises continuously contacting elemental nickel having a surface area of at least about 800 square centimeters per gram of nickel, in a reaction medium comprising in percent by weight based upon the weight of the liquid in the reaction medium at least 50% L, at least 2% of an organic nitrile having 4-20 carbon atoms and at least 100 ppm Cl as an organochloridite while maintaining the temperature in °C. of the reaction within the range defined by a minimum temperature equal to $102-0.375\times(\%L)$ and a maximum temperature equal to $58.3+0.725\times(\%L)$.

2. The process of claim 1 wherein the concentration of L is maintained in the range of 70-92%.

3. The process of claim 2 wherein the concentration of organic nitrile is maintained in the range 6-12%.

4. The process of claims 1, 2 or 3 wherein the surface area of the nickel powder is maintained in the range 800-2000 square centimeters per gram of nickel and the concentration of chloridite is maintained in the range 150-300 ppm Cl.

5. The process of claim 1 wherein L is a ligand of the formula $P(OAr)_3$ where Ar is an aryl group of up to 18 carbon atoms.

6. The process of claim 4 wherein L is a ligand of the formula $P(OAr)_3$ where Ar is an aryl group of up to 18 carbon atoms.

* * * * *